United States Patent

Beoni

[11] Patent Number: 5,814,104
[45] Date of Patent: Sep. 29, 1998

[54] MIDDLE EAR OSSICULAR CHAIN PROSTHESIS, WITH A POROUS HYDROXYLAPATITE FLANGE

[76] Inventor: Franco Beoni, Via Venturini 6, 29100 Piacenza, Italy

[21] Appl. No.: 616,512

[22] Filed: Mar. 19, 1996

Related U.S. Application Data

[63] Continuation-in-part of Ser. No. 202,800, Feb. 28, 1994, abandoned.

[30] Foreign Application Priority Data

Nov. 26, 1993 [IT] Italy ................. MI93A2504

[51] Int. Cl.⁶ .................. A61F 2/18; A61F 2/28
[52] U.S. Cl. ........................... 623/10; 623/16
[58] Field of Search .................... 623/10, 16

[56] References Cited

U.S. PATENT DOCUMENTS 2,206,807  7/1940  Christe .
3,473,170  10/1969  Haase et al. .
4,281,419  8/1981  Treace ........................................ 623/16
4,601,723  7/1986  McGrew .
4,871,364  10/1989  Bays et al. ................................ 623/10
4,936,305  6/1990  Ashtiani et al. ......................... 600/12
4,957,507  9/1990  Lenkauskas .............................. 623/10
4,969,913  11/1990  Ojima ....................................... 623/16
4,976,736  12/1990  White et al. ............................. 623/16
5,180,391  1/1993  Beoni ....................................... 623/10
5,220,918  6/1993  Heide et al. .............................. 623/10
5,554,188  9/1996  Prescott .................................... 623/10
5,578,086  11/1996  Prescott .................................... 623/10
5,728,157  3/1998  Prescott .................................... 623/10
5,728,395  3/1998  Ohtsuka et al. .......................... 623/16

*Primary Examiner*—Paul B. Prebilic
*Attorney, Agent, or Firm*—Ladas & Parry

[57] ABSTRACT

In the middle ear ossicular chain prosthesis, the tympanic end part (12), a face (14) of which makes contact with the tympanic membrane, is formed of ceramic hydroxylapatite. The constituent ceramic hydroxylapatite of the tympanic end part is porous with a pore size of between 100 and 400 micrometres.

24 Claims, 3 Drawing Sheets

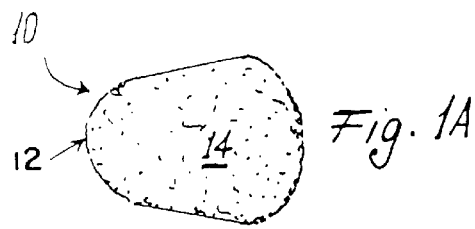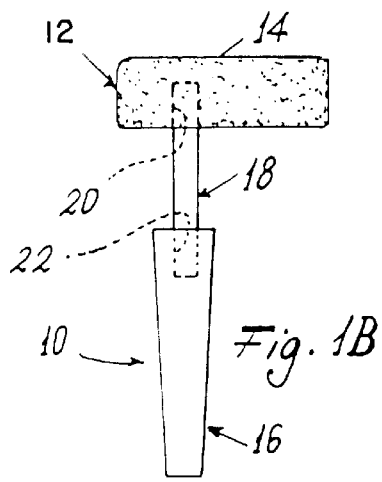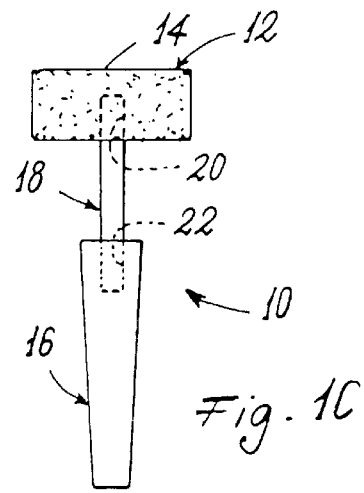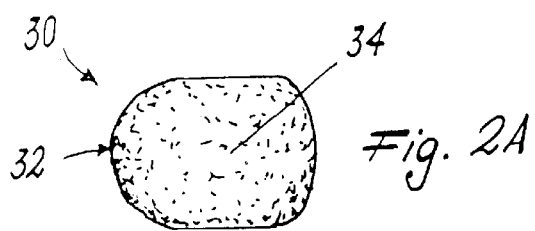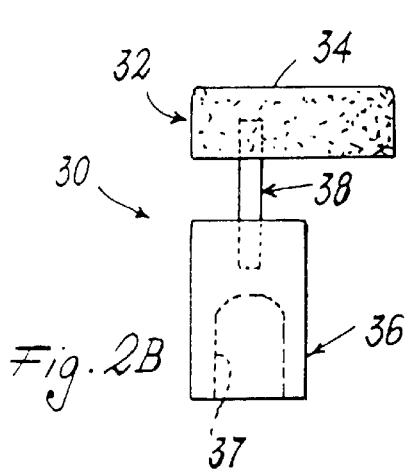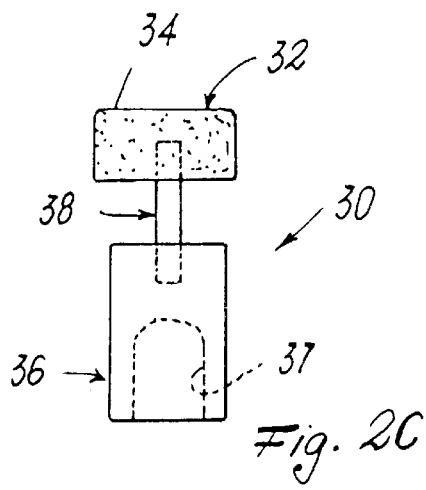

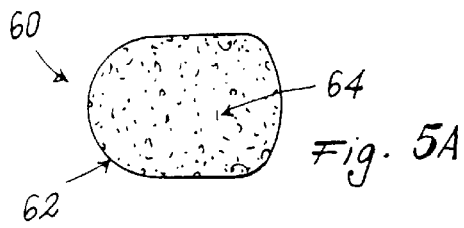
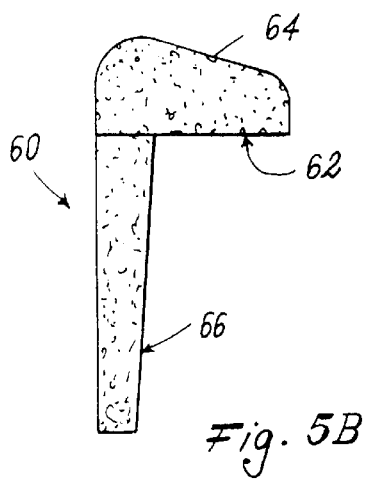
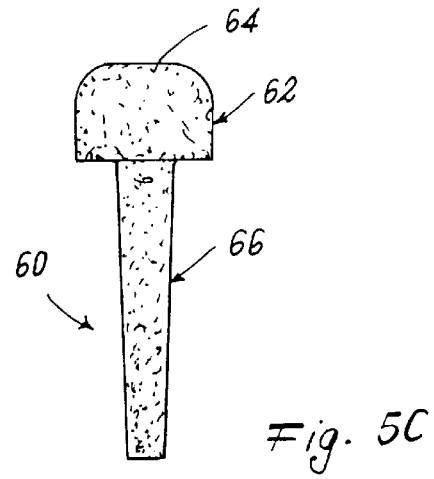
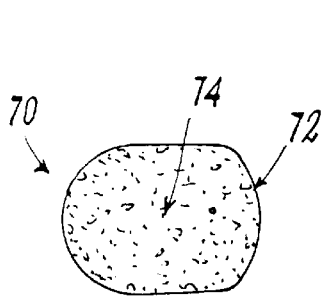
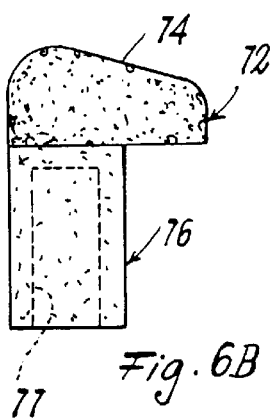
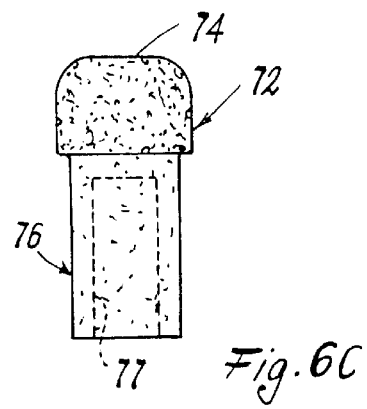
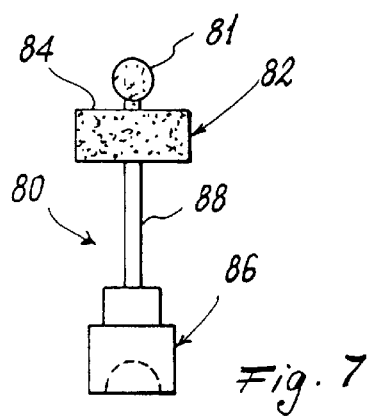
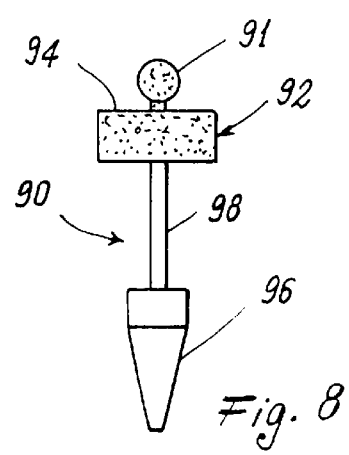

MIDDLE EAR OSSICULAR CHAIN PROSTHESIS, WITH A POROUS HYDROXYLAPATITE FLANGE

CROSS REFERENCE TO RELATED APPLICATION

This application is a Continuation-in-Part of U.S. patent application Ser. No. 08/202,800, filed on Feb. 28, 1994, herein incorporated by reference which is now abandoned.

DESCRIPTION OF THE FIELD OF THE INVENTION

This invention relates to prostheses for totally or partially replacing the ossicular chain of the middle ear.

Many implants have been already proposed for reconstructing the ossicular chain of the middle ear, ranging from the oldest and in practice totally unachievable, such as that conceived by Christe (U.S. Pat. No. 220,680,7 filed in 1939), to the most recent and realistic attempts, such as that of Haase (U.S. Pat. No. 347,317,0 filed in 1967).

This latter attempts to fix the prosthesis to the auditory tube and stapes, which in practice was also found unachievable.

Simpler prostheses were finally conceived and used, and are still used at the present time, such as that of Treace (U.S. Pat. No. 451,062,7).

This latter provides for attaching to the tympanic membrane, using porous polyethylene, material already used (and carrying the registered trademark PLASTIPORE) for constructing ossicular chain prostheses.

If porous polyethylene is brought into contact with well vascularized tissues it is pervaded by newly formed small vessels which enter the pores to create a physical bond between the living tissue and the polyethylene. The tympanic membrane is unfortunately very thin and perforates easily as a result of an inflammatory reaction caused by molecules yielded by the polyethylene and not recognized by the body as its own. A practical remedy to this drawback is stated in the Treace patent and consists of interposing a piece of cartilage tissue between the prosthesis flange and the tympanum. However by this means the porous polyethylene is no longer attached to the tympanic tissue, with the consequent possibility of displacement of the prosthesis, this occurring in a high percentage of cases.

The Trace prosthesis comprises a steel core the purpose of which is to stiffen the polyethylene to the advantage of sound transmission. This metal core also makes it possible to incline the prosthesis flange so that it is parallel to the tympanum under which it is placed. In this case the shaping of the prosthesis represents an improvement over the preceding Treace patent (U.S. Pat. No. 428,141,9).

McGrew (U.S. Pat. No. 460,172,3) describes a prosthesis extendable and inclinable as required, which economizes on the number of prostheses which the surgeon has to carry (the prostheses are usually in fixed lengths increasing by 0.5 mm steps). It is fixed to the tympanum by interposing a cartilage disc secured to the metal flange of the prosthesis by suture stitches. These can be either reabsorbable or permanent. As is known, reabsorbable stitches dissolve within a maximum period of 2–3 months whereas permanent stitches (silk or artificial polymers) are not left within the body as they can cause suppuration. That such an arrangement is unrealistic is proved by the fact that the prosthesis has never been available commercially and has not been used in surgical practice.

Lenkaukas (U.S. Pat. No. 495,750,7) describes a prosthesis consisting of a metal wire with a hydroxylapatite disc in contact with the tympanic membrane. This was the first time that ceramic dense hydroxylapatite had been used in prostheses of this type, this material being currently normally used for constructing most ossicular prostheses.

The columellar prosthesis forming part of the artificial middle ear described in U.S. Pat. No. 518,039,1, in the name of the present applicant, comprises two pieces of ceramic dense hydroxylapatite joined together by a platinum articulated joint. The columellar prosthesis is rigid to optimize sound transmission. It can be inclined or bent bayonet-wise and is mechanically connected to the tympanic prosthesis by an apophysis. Three years after the operation 21 patients to whom this artificial middle ear was fitted demonstrate the validity of this system, having not only recovered their hearing but also shown no symptom of inflammation or reject. In those cases in which the tympanic membrane is intact or has been reconstructed with biological tissue in a previous operation, said artificial columellar middle ear prosthesis can still be used by inserting said spherical apophysis into a hole of smaller size than the apophysis, formed in the tympanic membrane.

SUMMARY OF THE INVENTION

The object of the present invention is to solve in a simple manner the problem of connecting an ossicular chain prosthesis to the original tympanum or to the new tympanum constructed of biological tissue without perforating the tympanum.

Before describing the method of the present invention for solving this problem it should be noted, for a better understanding of the solution, that the middle ear consists of the tympanic cavity which is closed upperly by the tympanum and is traversed by the ossicular chain comprising the malleus, incus and stapes. The middle ear receives the sound wave via the tympanum and transmits it to the internal ear via the ossicular chain. Infections of the middle ear (otitis) can destroy part or the whole of the ossicular chain and/or perforate the tympanum. The ossicles are reconstructed by prostheses which are interposed, as required, between the malleus and stapes (incus replacement), between the malleus and stapes footplate (replacement of the incus and part of the stapes), or between the tympanum and stapes or its footplate (replacement of malleus, incus and, in the second case, also part of the stapes). In these two latter cases, as the malleus is replaced the tympanic end of the prosthesis rests against the tympanum, or against the newly formed tympanum if a perforated tympanum has been reconstructed with biological tissue in a previous operation. During the whole history of ear surgery this type of prosthesis in contact with the tympanum (or newly formed tympanum) has suffered from two problems which have remained unsolved:

The constituent material of the prosthesis does not adhere to the tympanum, so that the prosthesis shifts from the position in which it is placed by the surgeon, so interrupting sound transmission; The constituent material of the prosthesis induces phlogistic reactions in the tympanic tissue, which result in perforation of the tympanic membrane.

As already stated, the problem of adhesion of the ossicular prosthesis to the tympanic membrane appeared to be solved by using porous polyethylene (known under the registered trademark of Plastipore-Policel). This material has a porosity which attracts cellular elements from the tympanum into its cavities, to achieve a good physical bond. As also stated and as found in surgical practice, this material induces inflammatory reactions which often result in re-perforation of the tympanic membrane. In this respect porous polyethylene is classified as bioinert (i.e. with minimum transfer of molecules and with minimum phlogistic response), which is sufficient to cause perforation of a tissue as thin as the tympanic membrane in time. The stated expedient, now forming part of surgical practice, of interposing a layer of cartilage between the prosthesis and tympanum effectively prevents re-perforation, but does not allow a bond to be achieved with the prosthesis, which can be fixed only to a vascularized tissue, which the interposed piece of cartilage is not.

The problem of tympanic membrane re-perforation was solved with the introduction of ceramic dense hydroxylapatite. This is a biocompatible material, ie it yields molecular components recognized by the body as its own, so that there is no phlogistic response. For this reason hydroxylapatite prostheses, in use for some years, are used without interposing cartilage.

Besides being biocompatible, hydroxylapatite is bioactive, in the sense that it demonstrates a surface chemical activity which in about 2 months leads to a solid bond with the bone. This bond develops with non-osseous tissues such as the tympanic membrane only later and to a lesser extent. The result is that a dense hydroxylapatite prosthesis frequently shifts from the position in which it was located by the surgeon, so interrupting sound transmission. Many surgeons have consequently returned to reconstructing the ossicular chain using cartilage blocks shaped during surgery. This results in a number of further problems, mainly: a longer time required for the surgery; the need to construct the prosthesis at that given moment on an artesan basis and hence with considerable inaccuracy, the result depending in any event on the manual ability of the surgeon; reabsorption of the cartilage with time; and the danger of infection transmitted by tissue taken from a cadaver.

Returning to the present invention, the stated object is attained according to the invention by an ossicular chain prosthesis in which that end part of the prosthesis facing the tympanic membrane consists of ceramic hydroxylapatite and comprises a face arranged to make contact with the tympanic membrane, characterised in that the constituent ceramic hydroxylapatite of the tympanic end part is porous with a pore size of between 100 and 400 micrometres.

This porosity has proved ideal for stimulating the so-called fibro-osteoconduction phenomenon by which cellular elements of the tympanic tissue enter the pores to bond the prosthesis within only 3–5 days. The phenomenon is analogous to that which takes place with porous polyethylene, with the difference that hydroxylapatite is biocompatible and therefore induces no phlogistic response by the tympanic tissue, with the result that the tympanum does not perforate. In addition once the prosthesis has bonded to the tympanum by the described copenetration, the second type of bond deriving from the bioactivity of the hydroxylapatite can develop, this bond developing in about 2 months and occurring only if the flange is fixed to the tympanum, a condition which is ensured by said previously generated fibroconductive bond.

It has proved particularly convenient for the purpose of achieving a good bond between the tympanic tissue and hydroxylapatite flange to restrict the pore size range to about 200 micrometres.

The use of porous hydroxylapatite has the further advantage of a much lower weight than a similar prosthesis of dense hydroxylapatite, so that it is subjected to substantially lesser gravitational and inertial forces.

The remaining part of the ossicular chain prosthesis according to the present invention can be of known type.

In particular, that end part of the prosthesis facing the internal ear can either also be of porous ceramic hydroxylapatite, possibly integral with the tympanic end part, or be of conventional dense ceramic hydroxylapatite or bioinert rigid plastics material (such as polyethylene or polytetrafluoro-ethylene), this latter end part being connected to the tympanic end part by a connection element of bioinert material which is rigid but can be bent, such as a segment of platinum wire, the two ends of which are respectively fixed to the two said end parts in various ways.

The invention will be more apparent from the description of some embodiments thereof given hereinafter by way of example only. The description makes reference to the accompanying drawings.

BRIEF DESCRIPTION OF THE DRAWINGS

FIGS. 1A, 1B and 1C show a first embodiment of the prosthesis according to the invention in the form of orthogonal projections;

FIGS. 2A, 2B and 2C are three orthogonal projections of a second embodiment;

FIGS. 5A, 5B and 5C are orthogonal projections of a fifth embodiment;

FIGS. 6A, 6B and 6C are orthogonal projections of a sixth embodiment;

FIG. 7 is a side view of a seventh embodiment shown on a reduced scale; and

FIG. 8 is a side view of an eighth embodiment also shown on a reduced scale.

DETAILED DESCRIPTION

Figure 3A:
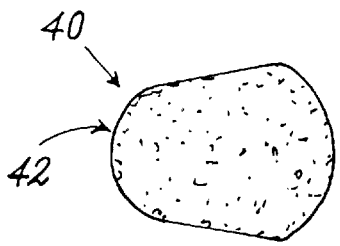
FIGS. 3A, 3B and 3C are orthogonal projections of a third embodiment.

From FIGS. 1A, 1B and 1C it can be seen that the middle ear prosthesis 10 comprises an upper flange 12 of the already specified porous ceramic hydroxylapatite. The upper face 14 of this flange is intended to make contact with the tympanic membrane (or newly formed tympanic membrane). Consequently by the effect of the described fibro-osteoconduction the flange 12 will already be bonded to the tympanic membrane 3–5 days after the application of the prosthesis.

The prosthesis 10 also comprises a columella 16 of inverted frusto-conical shape formed of dense hydroxylapatite. The distal end part of the columella 16 is preferably coated with medical grade silicone to avoid the danger of its fixing to the edges of the oval fossa.

The columella 16 is joined to the flange 12 by a segment 18 of platinum wire. The two ends of this platinum segment are inserted under slightly forced conditions into relative conjugate cavities 20 and 22 provided in the flange 12 and in the columella 16 respectively, or embedded into these latter during their formation, or glued into the relative cavities. The platinum segment 18 can be suitably bent during the surgery involved in applying the prosthesis both to reproduce the angle between the tympanum or newly formed tympanum and the columella, and to misalign the columella in order to view the oval window during the positioning of the free end of the columella on the footplate of the stapes.

Apart from a slight difference in the plan shape of the flange and a different configuration of the columella 36 to adapt it to the case in which the whole stapes is intact, the prosthesis 30 shown in FIGS. 2A, 2B and 2C is otherwise conceptually identical to the aforedescribed prosthesis 10. In this case the columella 36, of overall cylindrical shape, comprises in its lower face a cavity 37 of rounded base into which the capitellum of the stapes is inserted.

Figure 3B:
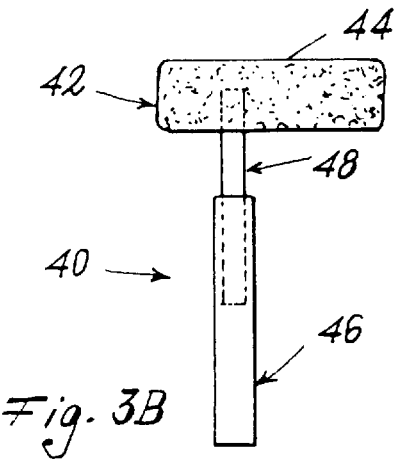
Figure 3C:
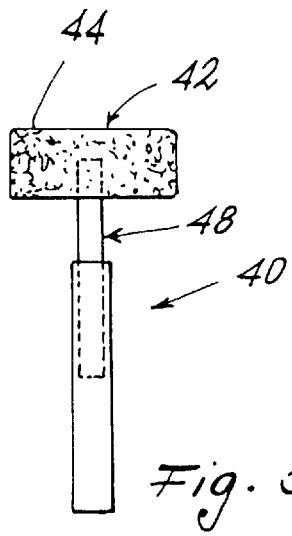

The prosthesis 40 of FIGS. 3A, 3B and 3C is similar to that of FIGS. 1A, 1B and 1C with the only difference that the cylindrical columella 46 is of biocompatible rigid plastics, such as Teflon (registered trademark), polyethylene or medical grade silicone. In this case the columella 46 is given the maximum forseeable required length, as it can be shortened by cutting off an end portion with a cutting means, to adapt its length to the specific case.

Figure 4A:
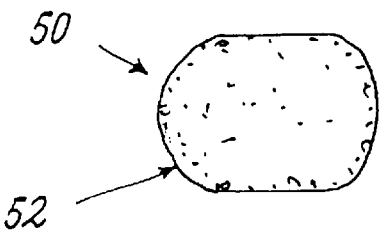
FIGS. 4A, 4B and 4C are orthogonal projections of a fourth embodiment.
Figure 4B:
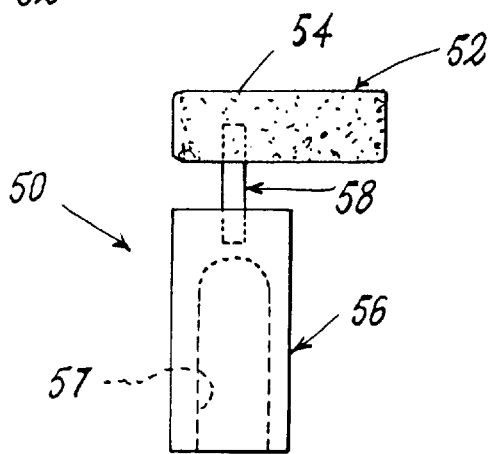
Figure 4C:
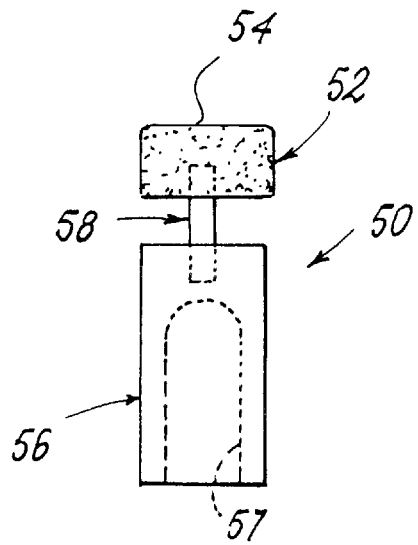

Following the same criterion as the preceding case, the prosthesis 50 shown in FIGS. 4A, 4B and 4C differs from the prosthesis of FIGS. 2A, 2B and 2C in that its columella 56 is of biocompatible rigid plastics, so that this columella can also be shortened as required by the specific case.

FIGS. 5A, 5B and 5C show a prosthesis 60 as a single piece of porous hydroxylapatite. The inclination of the upper surface 64 of the flange 62, its shape and the fact that the columella 66 is eccentric mean that the oval window can be viewed during the positioning of the prosthesis. By coating the free end of the columella 66, which could come into contact with the bone, with medical grade silicone prevents any danger of the columella becoming fixed to the edges of the oval fossa and to the facial wall. Rounding the edges of the top of the flange 62 prevents contact between sharp corners and the tympanum or newly formed tympanum. The thickness of the flange 62 is sufficient to enable a groove to be made for housing the handle of the malleus if this has been preserved. This housing can be formed during the construction of the prosthesis or at the moment of its application. For this purpose a diamond-set cutter can be used under continuous irrigation.

The prosthesis 70 of FIGS. 6A, 6B and 6C differs from the prosthesis 60 of the preceding case merely in the shape of the columella 76, the cavity 77 of which is able to receive the capitellum of the stapes.

FIGS. 7 and 8 show prostheses (80 and 90 respectively) which differ from those of FIGS. 1A, 1B, 1C and 2A, 2B, 2C substantially only by the presence of an apophysis 81 and 91 respectively, of the type described in U.S. Pat. No. 518,039, 1. As already stated, the apophysis 81, 91 is forcibly inserted into a hole previously formed in the tympanum or new tympanum of diameter slightly less than that of the apophysis. This enables the tympanic membrane to be maintained adhering to the upper surface 84, 94 respectively of the flanges 82 and 92.

Porous, non-resorbable hydroxyapatite can be produced as follows: Mixing for 30 minutes in a mixer powders having different specific gravity powdered hydroxyapatite (such as that produced by MERCK, Germany) with granules of a substance capable of being completely decomposed in $H_2O$ and $CO_2$ when heated at a temperature lower than the ceramizing temperature of the hydroxyapatite. These granules can be, for instance, castor tartanic acid or granular polyethylene and should preferably have a size between 130 and 500 micrometers.

The following two steps are the same as those for producing the known ceramized non-porous hydroxyapatite, and particularly: 1. Pressing the mixture in a die which is previously coated with stearic acid dissolved in ethyl alcohol, and 2. Pressing isostatically the resulting element under vacuum condition up to 100 $MN/m^2$.

Lastly, there is the following further step: Heating the element obtained in a humid oxygen atmosphere, increasing the temperature by 100° C./hour up to the ceramizing temperature of the hydroxyapatite (1200° C.). During heating (from 200° to 400° C.) the decomposition of the abovementioned grains occurs. The vaporization of the grains creates a porous structure, the pores having an ideal size for stimulating the growth of connective tissue in them. The pores thus obtained have a size between 100 and 400 micrometers, since there is a contraction in the pores of about 25% during ceramization.

I claim:

1. An ossicular chain prosthesis for a middle ear, the prosthesis having a first end part for facing a tympanic membrane, at least a portion of the end part being for contacting the tympanic membrane and being comprised of ceramic hydroxylapatite, the ceramic hydroxylapatite being nonresorbable, porous and having a pore size of between 100 and 400 micrometers.

2. A prosthesis as claimed in claim 1, wherein the prosthesis has a second end part for facing the internal ear, the second end part being connected to the first end part by a connection element of bioinert material which is rigid but can be bent.

3. A prosthesis as claimed in claim 2, wherein the connection element is a segment of platinum wire.

4. A prosthesis (10; 30; 80; 90) as claimed in claim 2, wherein that end part (16; 36; 86; 96) of the prosthesis facing the internal ear is of dense ceramic hydroxylapatite.

5. A prosthesis as claimed in claim 2, wherein the second end part comprises a biocompatible rigid plastics material.

6. A prosthesis as claimed in claim 5, wherein the second end part has a length enabling it to be shortened with a cutting means.

7. A prosthesis as claimed in claim 5, wherein the bioinert rigid plastics material is polytetrafluoroethylene or polyethylene.

8. A prosthesis as claimed in claim 1, wherein the prosthesis is comprised entirely of porous ceramic hydroxylapatite.

9. A prosthesis (80; 90) as claimed in claim 1, wherein that face of the tympanic end part (82; 92) which is to make contact with the tympanum comprises an apophysis (81; 91) to be inserted into a hole previously formed in the tympanum to connect the prosthesis to the tympanum.

10. A prosthesis as claimed in claim 1, wherein the face of the end part facing the tympanic membrane has rounded edges.

11. A prosthesis (60; 70) as claimed in claim 2, wherein that face (64; 74) of the tympanic end piece (62; 72) facing the tympanum has rounded edges.

12. A prosthesis (6G; 70) as claimed in claim 3, wherein that face (64; 74) of the tympanic end piece (62; 72) facing the tympanum has rounded edges.

13. A prosthesis (60; 70) as claimed in claim 4, wherein that face (64; 74) of the tympanic end piece (62; 72) facing the tympanum has rounded edges.

14. A prosthesis (60; 70) as claimed in claim 5, wherein that face (64; 74) of the tympanic end piece (62; 72) facing the tympanum has rounded edges.

15. A prosthesis (60; 70) as claimed in claim 6, wherein that face (64; 74) of the tympanic end piece (62; 72) facing the tympanum has rounded edges.

16. A prosthesis (60; 70) as claimed in claim 7, wherein that face (64; 74) of the tympanic end piece (62; 72) facing the tympanum has rounded edges.

17. A prosthesis (60; 70) as claimed in claim 8, wherein that face (64; 74) of the tympanic end piece (62; 72) facing the tympanum has rounded edges.

18. A prosthesis (60; 70) as claimed in claim 9, wherein that face (64; 74) of the tympanic end piece (62; 72) facing the tympanum has rounded edges.

19. A prosthesis as claimed in claim 2, wherein the second end part has a length enabling it to be shortened with a cutting means.

20. A prosthesis as claimed in claim 1, wherein the pore size is about 200 micrometers.

21. A prosthesis as claimed in claim 2, wherein the pore size is about 200 micrometers.

22. A prosthesis as claimed in claim 5, wherein the pore size is about 200 micrometers.

23. A prosthesis as claimed in claim 6, wherein the pore size is about 200 micrometers.

24. A prosthesis as claimed in claim 19, wherein the pore size is about 200 micrometers.

* * * * *